United States Patent
Arnold et al.

(10) Patent No.: US 12,045,367 B1
(45) Date of Patent: Jul. 23, 2024

(54) SYSTEMS AND METHODS FOR USER AUTHENTICATION USING HEALTH INFORMATION

(71) Applicant: United Services Automobile Association (USAA), San Antonio, TX (US)

(72) Inventors: Wesley Allen Arnold, Boerne, TX (US); Michael A. Belko, Boerne, TX (US); Steven K. Dunlap, Boerne, TX (US); Sharon Kay Haverlah, Bulverde, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 313 days.

(21) Appl. No.: 17/390,133

(22) Filed: Jul. 30, 2021

Related U.S. Application Data

(60) Provisional application No. 63/058,925, filed on Jul. 30, 2020.

(51) Int. Cl.
  G06F 21/62    (2013.01)
  G06F 16/25    (2019.01)
  G06F 21/32    (2013.01)
  G06N 20/00    (2019.01)
  G16H 10/60    (2018.01)

(52) U.S. Cl.
  CPC ........ G06F 21/6245 (2013.01); G06F 16/258 (2019.01); G06F 21/32 (2013.01); G06N 20/00 (2019.01); G16H 10/60 (2018.01)

(58) Field of Classification Search
  CPC .... G06F 21/6245; G06F 16/258; G06F 21/32; G06N 20/00; G16H 10/60
  USPC .............................................................. 726/28
  See application file for complete search history.

(56) References Cited

U.S. PATENT DOCUMENTS

| | | | |
|---|---|---|---|
| 6,014,081 A | 1/2000 | Kojima et al. | |
| 10,762,183 B1 * | 9/2020 | Charan | G06F 21/40 |
| 2004/0225200 A1 | 11/2004 | Edmundson et al. | |
| 2005/0125258 A1 | 6/2005 | Yellin et al. | |
| 2006/0149140 A1 | 7/2006 | Eldridge | |
| 2007/0004969 A1 | 1/2007 | Kong et al. | |
| 2007/0156453 A1 | 7/2007 | Frielinghaus et al. | |

(Continued)

OTHER PUBLICATIONS

"A Car That Takes Our Puse"; White; Nov. 28, 2012; Wall Street Journal (Year: 2012).
"Ford Wants Your Next Car to Monitor Your Vital Signs as You Drive"; Boyle; May 19, 2011; Popular Science (Year: 2011).
HIMSS Board of Directors; "Definition of Interoperability"; HIMSS; Apr. 5, 2013.

(Continued)

*Primary Examiner* — Jacob Lipman
(74) *Attorney, Agent, or Firm* — Fletcher Yoder, P.C.

(57) ABSTRACT

The present disclosure is related to a system that may include a first computing device and a second computing device. The first computing device may send a request for identification data corresponding to one or more health properties associated with a user. The second computing device may receive the request for the identification data. In response to receiving the request, the second computing device may retrieve health data acquired by one or more sensors for monitoring the one or more health properties that correspond to the user and stored in a memory. The first computing device may receive the health data sent from the second computing device and authenticate an identity of the user based on the health data.

19 Claims, 4 Drawing Sheets

(56) References Cited

U.S. PATENT DOCUMENTS

| | | |
|---|---|---|
| 2008/0021730 A1 | 1/2008 | Holla et al. |
| 2009/0132460 A1 | 5/2009 | Alemi |
| 2009/0209830 A1 | 8/2009 | Nagle et al. |
| 2011/0245633 A1 | 10/2011 | Goldberg et al. |
| 2012/0221345 A1 | 8/2012 | McClure et al. |
| 2014/0052464 A1 | 2/2014 | Ray |
| 2015/0326557 A1 | 11/2015 | Teramura et al. |
| 2015/0370994 A1 | 12/2015 | Madan et al. |
| 2016/0371786 A1 | 12/2016 | Kusens et al. |
| 2017/0043089 A1* | 2/2017 | Handler ............... G16H 40/63 |
| 2019/0386988 A1* | 12/2019 | Segura Perales ...... A61B 5/117 |
| 2020/0221969 A1* | 7/2020 | Ram ....................... H01L 31/08 |
| 2021/0241926 A1* | 8/2021 | Chor ....................... H04W 4/70 |

OTHER PUBLICATIONS

"Step 5: Achieve Meaningful Use Stage 2 Patient Ability to Electronically View, Download & Transmit (VDT) Health Information"; http://www.healthit.gov/providers-professionals/achieve-meaningful-use/core-measures-2/patient-ability-electronically-view-download-transmit-vdt-health-information; Feb. 24, 2014; last accessed Jan. 6, 2016.

Dullabh, P. MD; Adler-Milstein, J. PhD; Hovey, L. MS; JHA, A. MD MPH; "Final Report Key Challenges to Enabling Health Information Exchange and How States Can Help"; NORC; Aug. 2014.

"The Top 5 roadblocks HIEs face"; http://www.govhealthit.com/news/top-5-roadblocks-hies-face; Nov. 14, 2011; last accessed Jan. 6, 2016.

\* cited by examiner

SYSTEMS AND METHODS FOR USER AUTHENTICATION USING HEALTH INFORMATION

CROSS-REFERENCE TO RELATED APPLICATION

This application claims priority to and the benefit of U.S. Provisional Application No. 63/058,925, entitled "SYSTEMS AND METHODS FOR USER AUTHENTICATION USING HEALTH INFORMATION," filed Jul. 30, 2020, which is hereby incorporated by reference in its entirety for all purposes.

BACKGROUND

The present disclosure relates generally to providing user authentication using health information. More specifically, the present disclosure relates to verifying user identity based on user's health information and providing multi-factor authentication for identity proofing.

This section is intended to introduce the reader to various aspects of art that may be related to various aspects of the present disclosure, which are described and/or claimed below. This discussion is believed to help provide the reader with background information to facilitate a better understanding of the various aspects of the present disclosure. Accordingly, it is understood that these statements are to be read in this light, and not as admissions of prior art.

Increasing data privacy concerns are driving new privacy regulations to protect personal data usage. In response to emerging privacy regulations, entities that hold users' (e.g., clients') personal data may be pressed to provide improved user authentication to protect users' personal data and comply with the new privacy regulations.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a system may include a first computing device and a second computing device. The first computing device may send a request for identification data corresponding to one or more health properties associated with a user. The second computing device may receive the request for the identification data. In response to receiving the request, the second computing device may retrieve health data acquired by one or more sensors for monitoring the one or more health properties that correspond to the user and stored in a memory. The first computing device may receive the health data sent from the second computing device and authenticate an identity of the user based on the health data.

In another embodiment, a method may include receiving identification data associated with a user and sending a request for health data to a wearable system based on the identification data. The wearable system may include multiple sensors configured to acquire the health data indicative of one or more health properties corresponding to the user. The method may also include receiving a set of electronic medical records based on identification data and determining an identity of the user based on one or more correlations between the health data and the set of electronic medical records. The method may further include sending a notification indicative of an authentication of the user to the wearable system in response to determining the identity of the user.

In yet another embodiment, a non-transitory, computer-readable medium storing computer-executable instructions is provided. The instructions, when executed by a processor, cause the processor to receive a first request to authenticate an identity of a user and to determine one or more health properties collectable from one or more sensors of a wearable system associated with the user. The instructions also cause the processor to send a second request to the wearable system to collect health data based on the one or more health properties, to receive the health data from the wearable system, and to determine the identity of the user based on the health data.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
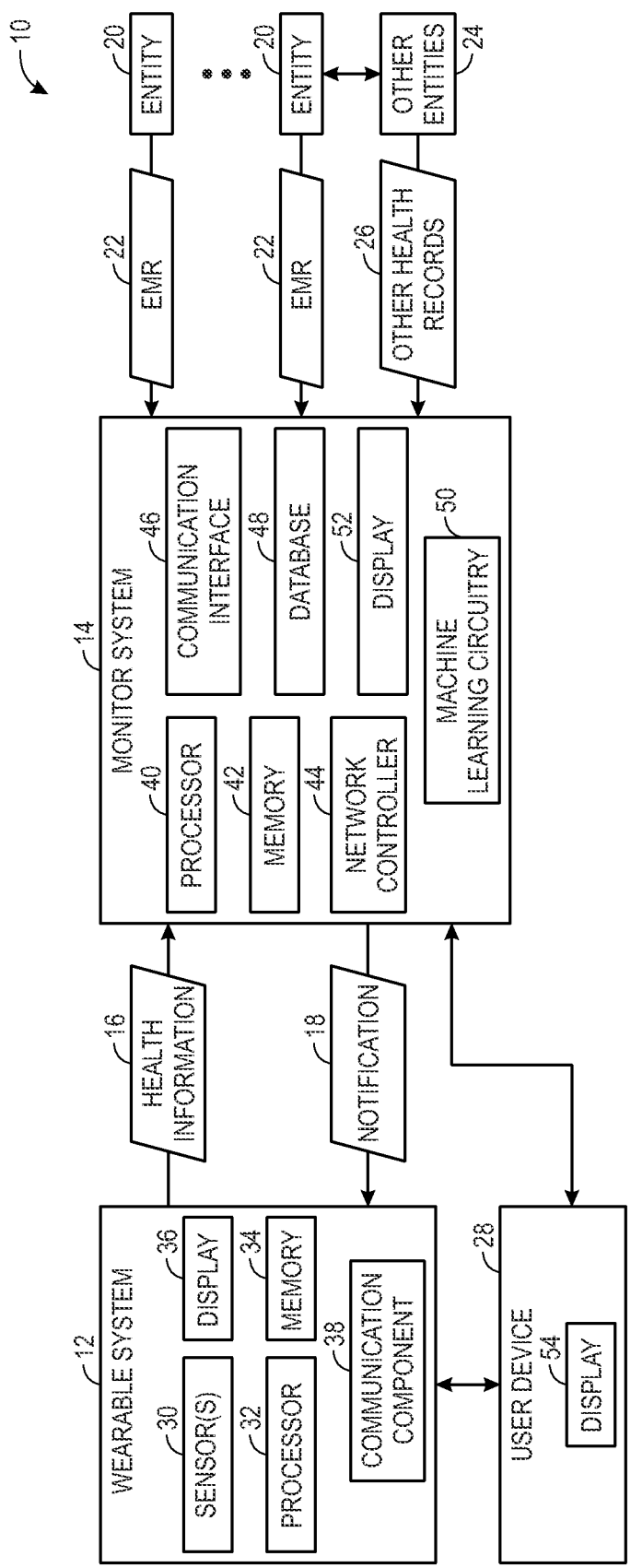
FIG. 1 illustrates a block diagram of a system for verifying user identity based on health-related information aggregated from various sources using a user authentication system, in accordance with embodiments described herein.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. It should be noted that the term "multimedia" and "media" may be used interchangeably herein.

Privacy regulations have become increasingly restrictive on personal data, particularly on personal health data. For example, according to the Health Insurance Portability and Accountability Act (HIPAA), there are 18 direct identifiers that are typically present in patient's medical records, such as names, geographic subdivisions smaller than a state (e.g. street address, city and ZIP code), all dates that are related to an individual (e.g., date of birth, admission), telephone numbers, fax numbers, email addresses, social security numbers, medical record numbers, health plan beneficiary numbers, and so on, that are to remain private and secure.

According to HIPAA, there are several acceptable ways to de-identify patient data, including a "safe harbor" option, in which the eighteen identifiers can be removed; a "statistical" option, in which a retained statistician determines which of the eighteen identifiers can be maintained without creating greater than a threshold risk percentage that the data could be re-identified; and a "limited data set" option, in which an entity can remove certain (e.g., sixteen) identifiers and protect what remains with special security precautions (e.g., with improved user authentication).

The entities (e.g., hospitals, physicians, other health care providers) that may hold the clients' health data may face increasing challenges to provide improved user authentications for their clients (e.g., patients). Some entities may be regulated to respond to client requests for personal health data available to the entities. Such client requests may include accessing certain personal health data without presenting a physical identification document. The physical identity document may be used to connect a person to information about the person (e.g., in a database). The photo and the possession of it is used to connect the person with the document. The connection between the identity document and the database may be based on personal information present on the document, such as the card bearer's full name, age, birth date, address, an identification number, card number, gender, citizenship and more. However, in some cases, using the identity document for identity verification is not feasible or desirable.

For example, a client (e.g., patient) may visit a hospital or a physician office. The client may be requested to show certain identification document (e.g., driver license card) that may be used prove the client's identity. However, the requested identification document may not be available at the time of visiting. With this in mind, in some embodiments, the client may use his/her health information (e.g., information collected from a wearable system) that may be communicatively connected to an admission system of the hospital or the physician's office to access his/her medical record. That is, the client's identity may be determined based on his/her health information without using his/her identification document.

With the foregoing in mind, in an embodiment, a wearable system may receive a request to collect certain type(s) of health information corresponding to a user. The request may include a list of health information to be collected. Based on the request, the wearable system may determine whether the requested health information is available. If the requested health information is available, the wearable system may collect and transmit the health information to a monitoring system. The monitoring system may receive the health information from the wearable system via a communication interface. Based on certain regulation criteria (e.g., direct identifiers described in HIPAA), the monitoring system may filter the health information to exclude certain personal identifiers. Further, the monitoring system may receive user identification data from the user and retrieve user's electronic medical record (EMR) based on the user identification data. Based on one or more correlations between the health information and the EMR, the monitoring system may determine user identity. Further, the monitoring system may generate a notification indicative of authentication of the user. The notification may then be sent to the wearable system.

In addition to verifying the user identity using health information collected from a wearable system, the monitoring system may also provide a multi-factor user authentication mechanism for verifying the user's identity by requesting multiple credentials (e.g., dynamically changed biomedical information and additional security questions). A user device may be used for providing additional credentials. The extra layers of security added by the multi-factor user authentication mechanism may provide improved protections for user's privacy data (e.g., against malicious use of the user's personal information), while complying with privacy-related regulations such as HIPAA. Additional details with regard to analyzing privacy data exposure, along with other technologies for consolidating privacy data exposure associated with the clients/users into privacy reports, will be discussed in detail below with reference to FIGS. 1-4.

By way of introduction, FIG. 1 illustrates a block diagram of a system for verifying a user's identity based on health-related information aggregated from various sources using a user authentication system 10. The user authentication system 10 may include a wearable system 12, a monitoring system 14, one or more entities 20, other entities 24, and a user device 28. The wearable system 12, the monitoring system 14, the one or more entities 20, the other entities 24, and the user device 28 may communicate with each other using a variety of communication protocols. The communication protocols may include Open Database Connectivity (ODBC), TCP/IP Protocol, Distributed Relational Database Architecture (DRDA) protocol, Database Change Protocol (DCP), HTTP protocol, Bluetooth, Wi-Fi, Near Field Communication (NFC), other suitable current or future protocols, or combinations thereof.

Through the communications using the above-mentioned protocols, the user authentication system 10 (e.g., the monitoring system 14) may aggregate health-related information regarding a user (e.g., a patient) and determine the user's identity based on the aggregated health-relation information. For example, the wearable system 12 may collect a certain type of health information of the user and send the health information 16 to the monitoring system 14. The monitoring system 14 may send a notification 18 (e.g., notification related to the user's identity) to the wearable system 12. The monitoring system 14 may further retrieve the user's Electronic Medical Record (EMR) 22 from the one or more entities 24. The EMR 22 may be similar to the EMR described in U.S. patent application Ser. No. 14/989,702, entitled "ELECTRONIC MEDICAL RECORD TRANSFER SYSTEMS AND METHODS", filed Jan. 6, 2016, which is incorporated by reference in its entirety for all purposes. In some embodiments, the monitoring system 14 may gather other health records 26 from other entities 24 that may provide other health-related services (e.g., fitness, diet, and nutrition). In some embodiments, the user device 28 (e.g., smartphone, tablet, electronic glass, laptop) may provide additional information to the monitoring system 14 for determining the user identity. The user device 28 may receive/send information (e.g., certain notifications, requests) from/to the monitoring system 14 and/or the wearable system 12.

The wearable system 12 may include any suitable wearable device (e.g., smart electronic devices with microcontrollers) that may be worn or in contact with human skin to continuously and closely monitor a user's activities without interrupting or limiting the user's activities (e.g., motions). The wearable device(s) may use sensors to detect, analyze, and transmit personal information associated with the user. The sensors may include motion sensors, thermal sensors, temperature sensors, vision and imaging sensors, biomedical sensors, proximity sensors, pressure sensors, position sensors, electrical sensors, optical sensors, photoelectric sensors, contact and/or non-contact sensors, and the like.

In some embodiments, the wearable device(s) in the wearable system 12 may monitor the user's health condition using biomedical sensors. The biomedical sensors may be used to collect health information of the user, including, but not limited to, pulse, heart rate, blood pressure, calories burned, blood sugar level, steps walked, exercising time, seizures, physical strain, biochemical release, and the like. For example, the biomedical sensors may detect medically relevant parameters, such as heart rate, body temperature, skin response, and muscle movements. Such biomedical sensors may include heart rate sensors (e.g., electrical and/or optical), blood pressure sensors, heart sound sensors, oxygen and carbon dioxide sensors, blood flow sensors, respiration sensors, Electromyography (EMG) sensors, galvanic skin response (GSR) sensors, fingerprint sensors, and so on.

As illustrated, the wearable system 12 may include one or more sensors 30, a processor 32, a memory 34, a display 36, and a communication component 38. As described above, the wearable system 12 may use the one or more sensors 30 to sense and collect certain type(s) of health information of the user. The collected health information may be processed by the processor 32 using instructions stored in the memory 34. The collected and/or processed health information may be stored into the memory 34 and viewed by the user via the display 36. At least a portion of the collected and/or processed health information, health information 16, may be transmitted in one packet or in separated packets via the communication component 38 to the monitoring system 14.

The processor 32 may receive a request to collect certain type(s) of health information. The request may include a list of health information to be collected. Based on the request, the processor 32 may determine whether the requested health information is available (e.g., health information from the one or more sensors 30 or stored in the memory 34). If the requested health information is available, the processor 32 may collect and transmit the health information (e.g., health information 16) to the monitoring system 14. In some embodiments, the processor 32 may coordinate with other wearable devices (e.g., watch, fitness tracker, pacemaker) to collect, organize, format, aggregate, integrate, or merge, and filter various health information. The health information 16 may be transmitted in one or more packets to the monitoring system 14. For example, the pulse and heart rate may be sent in one packet, while the blood function related parameters (e.g., pressure, flow rate, or blood sugar) may be transmitted in another packet.

The processor 32 may be any type of processor or microprocessor capable of executing computer-executable code. The processor 32 may include multiple processors that may perform certain operations that will be discussed in detail below with reference to FIG. 2.

The memory 34 may be any suitable articles of manufacture that can serve as media to store processor-executable code, data, or the like. These articles of manufacture may represent computer-readable media (e.g., any suitable form of memory or storage) that may store the processor-executable code used by the processor 32 to perform the presently disclosed techniques. The memory 34 may also be used to store data (e.g., health information acquired by the one or more sensors 30), various other software applications for analyzing the data, and the like. In some embodiments, the memory 34 may store certain medical history of the user (e.g., blood pressure and/or blood sugar measurement in certain period of time). The memory 34 may represent non-transitory computer-readable media (e.g., any suitable form of memory or storage) that may store the processor-executable code used by the processor 32 to perform various techniques described herein. It should be noted that non-transitory merely indicates that the media is tangible and not a signal.

The display 36 may operate to depict visualizations associated with software or executable code being processed by the processor 32. In an embodiment, the display 36 may be a touch display capable of receiving inputs from the user of the wearable system 12. The display 36 may be any suitable type of display, such as a liquid crystal display (LCD), plasma display, or an organic light emitting diode (OLED) display, for example. Additionally, in an embodiment, the display 36 may be provided in conjunction with a touch-sensitive mechanism (e.g., a touch screen) that may function as part of a control interface for the wearable system 12.

The communication component 38 may operate to support mobile wearable communications. The wearable system 12 may communicate, via the communication component 38, with the monitoring system 14 and/or the user device 28 (e.g., smartphones, tablets, and laptops) in a client-server fashion or peer-to-peer fashion. The wearable system 12 may integrate one or more radio technologies for various applications (e.g., health monitoring) with small power consumption and low transmission delays. These devices can hence collect, interpret, transmit, and exchange data with the monitoring system 14, the user device 28, other wearable devices, and the Internet. Such data may be any type of transmittable data, including, but not limited to user's personal health information (e.g., biomedical data), social and contextual data, and the like. It should be noted that the components described above with regard to the wearable system 12 are exemplary components and the wearable system 12 may include additional or fewer components as shown.

As mentioned above, the monitoring system 14 may send a request to wearable system 12 to collect certain type(s) of health information. In response to the request, the wearable system 12 may use the one or more sensors 30 to acquire and transmit the health information 16 to the monitoring system 14. As illustrated, the monitoring system 14 may include a processor 40, a memory 42, a network controller 44, a communication interface 46 and one or more databases 48.

In some embodiments, the monitoring system 14 may include machine learning circuitry 50 and a display 52.

The processor 40 may receive the health information 16 from the wearable system 12 via the communication interface 46. Based on certain regulation criteria (e.g., direct identifiers described in HIPAA), the processor 40 may filter the health information 16 to exclude certain personal identifiers (e.g., birth date, address). Further, the processor 40 may receive user identification data (e.g., name) from the user and retrieve the user's EMR 22 based on the user identification data. Based on correlation (e.g., data similarity) between the health information 16 and the EMR 22, the processor 40 may determine the user's identity. The processor 40 may then generate the notification 18 indicative of an authentication of the user. The notification 18 may be sent, via the network controller 44, to the wearable system 12. In some embodiments, a notification similar to the notification 18 may be sent to the user device 28 and presented to the user via the display 54.

The processor 40 may be any type of computer processor or microprocessor capable of executing computer-executable code. The processor 40 may also include multiple processors that may perform certain operations that will be discussed in detail below with reference to FIGS. 3 and 4.

The memory 42 and the database 48 may be any suitable articles of manufacture that can serve as media to store processor-executable code, data, or the like. These articles of manufacture may represent computer-readable media (e.g., any suitable form of memory or storage) that may store the processor-executable code used by the processor 40 to perform the presently disclosed techniques. The memory 42 and the database 48 may also be used to store data described (e.g., health information 16, EMR 22, and other health records 26), various other software applications for analyzing the data, and the like. The memory 42 and the database 48 may represent non-transitory computer-readable media (e.g., any suitable form of memory or storage) that may store the processor-executable code used by the processor 40 to perform various techniques described herein. It should be noted that non-transitory merely indicates that the media is tangible and not a signal.

The network controller 44 may include hardware and/or software that orchestrate network functions. For example, the network controller 44 may monitor, operate, troubleshoot, and maintain data communications between the monitoring system 14 and other systems/devices (e.g., the wearable system 12, the one or more entities 20, the other entities 24, and the user device 28). As noted previously, the data communications may include user's personal data (e.g., health information 16, EMR 22, other health records 26, and user identification data). The user's personal data may contain privacy-related information (e.g., name, gender, age, race, address, phone number, email, medical condition, health-related information). The network controller 44 may be used to create secured connections (e.g., channels) between the monitoring system 14 and other systems/devices. The secured connections may prevent privacy data exposure related to hacking or compromising activities that may result in the privacy data becoming available to others, such as collecting, processing, disseminating, and invading privacy data without consent and/or authorization from the user.

The communication interface 46 may be an interface that may couple to other peripheral components, such as input devices (e.g., keyboard, mouse), sensors, input/output (I/O) modules, network devices, and the like. For example, the communication interface 46 may be communicatively coupled to the processor 40 and network controller 44.

The display 52 may operate to depict visualizations associated with software or executable code being processed by the processor 40. In an embodiment, the display 52 may be a touch display capable of receiving inputs from a user of the monitoring system 14. The display 52 may be any suitable type of display, such as a liquid crystal display (LCD), plasma display, or an organic light emitting diode (OLED) display, for example. Additionally, in an embodiment, the display 52 may be provided in conjunction with a touch-sensitive mechanism (e.g., a touch screen) that may function as part of a control interface for the monitoring system 14.

In some embodiments, the monitoring system 14 may include the machine learning circuitry 50 (e.g., circuitry used to implement machine learning algorithms or logic). Certain operations of the monitoring system 14, as described above, may be performed using the machine learning circuitry 50. For example, the processor 40 may determine the user's identity based on a correlation between the health information 16 and the EMR 22. The correlation may be determined through data analysis (e.g., analyzing data similarity) using the machine learning circuitry 50. In some embodiments, the machine learning circuitry 50 may access the health information 16 and the EMR 22 to identify correlations, patterns, or trends associated with the user. In some embodiments, the machine learning circuitry 50 may include algorithms and statistical models to perform a specific task with or without using explicit instructions. For example, a machine learning process may generate a mathematical model based on a sample of the clean data, known as "training data," in order to make predictions or decisions without being explicitly programmed to perform the task.

The machine learning circuitry 50 may implement different types of machine learning algorithms. In some embodiments, supervised machine learning algorithms may be implemented. For example, similarity learning is an algorithm of supervised machine learning that may be used to learn from examples using a similarity function that measures how similar or related two sets of data (e.g., one set of data related to the health information 16 and another set of data related to the EMR 22) are. In some embodiments, unsupervised learning may be implemented, for example when particular output types are not known. Unsupervised learning algorithms may take some test data (e.g., health-related data) that contains only inputs, and find structure in the data, like grouping or clustering of transaction data. The algorithms, therefore, learn from the test data that has not been labeled, classified or categorized. Instead of responding to feedback, unsupervised learning algorithms identify commonalities in the health-related data and react based on the presence or absence of such commonalities in each piece of the health-related data. It should be noted that the components described above with regard to the monitoring system 14 are exemplary components and the monitoring system 14 may include additional or fewer components as shown.

As mentioned above, the monitoring system 14 may retrieve the user's EMR (e.g., EMR 22) from the one or more entities 20 (e.g., hospitals, physicians, other healthcare providers). In some embodiments, the EMR 22 from some entities 20 may be in a different format from the EMR 22 as compared to the other entities 20. Thus, the EMR 22 may be reformatted into a common format (e.g., standard format). For example, the processor 40 may determine that the format of the retrieved EMR 22 and the accepted format used for determining the user identity are incompatible or different.

The processor 40 may normalize the format of the EMR 22 by retaining elements that are of interest while removing other undesired elements.

In some embodiments, the monitoring system 14 may retrieve other health records 26 associated with the user from the other entities 24. For example, the other health records 26 may include the user's health and fitness data, which may be stored in databases in the other entities 24 (e.g., fitness or recreation facilities). In some embodiments, the other health records 26 may be reformatted into the common format. Therefore, incompatible issues associated with other health records 26 that may be from different entities 24 may be removed.

The user device 28 may include any suitable type of computing device. In some embodiments, the user device 28 may be a portable computing device, such as a smartphone, tablet, electronic glass, wearable device (e.g., watch, fitness tracker, pacemaker), implanted computer, automotive computer, portable gaming platform, and so forth. In some embodiments, the user device 28 may also be a less portable type of computing device, such as a desktop computer, laptop computer, game console, smart appliance, and so forth.

In some embodiments, the user device 28 may collect additional health data, such as fitness tracking data (e.g., calories burned, steps walked, exercising time), pulse, heart rate, body temperature, skin response, muscle movements, blood pressure, blood sugar level, seizures, physical strain, biochemical release, and the like. In yet other embodiments, the user device 28 may collect image data, biometric data (e.g., fingerprint), and other types of data that may be used in the techniques describe herein.

In some embodiments, the user device 28 may provide additional information to the monitoring system 14 for determining the user identity. The user device 28 may receive/send information (e.g., certain notifications, requests) from/to the monitoring system 14 and/or the wearable system 12. Additional details with regard to the use of the user device 28 will be discussed below with reference to FIG. 4.

The user authentication system 10 may use one or more networks to facilitate the communications between the wearable system 12, the monitoring system 14, the one or more entities 20, the other entities 24, and the user device 28. Such networks may include any type of wired or wireless network, including but not limited to local area networks (LANs), wide area networks (WANs), wireless WANs (WWANs), wireless LANs (WLANs), mobile communications networks (e.g., 3G, 4G, 5G, Edge, etc.), and so forth. For example, the user authentication system 10 may use a local area network (LAN) that includes a variety of computing and network devices including, but are not limited to, switches, servers (e.g., processors), storage (e.g., memory), and routers. In some implementations, the communications between the above-mentioned systems/devices may be encrypted or otherwise secured. For example, the communications may employ one or more public or private cryptographic keys, ciphers, digital certificates, or other credentials supported by a security protocol, such as any version of the Secure Sockets Layer (SSL) or the Transport Layer Security (TLS) protocol. The user authentication system 10 may include restrictions and access rules established in order to relegate access to selected users (e.g., patients, physicians, healthcare providers, other health-related service providers, or regulatory representatives). In some embodiments, the user authentication system 10 may use a network that may actually be off premises (e.g., in a cloud or the like).

Although the wearable system 12, the monitoring system 14, the one or more entities 20, the other entities 24, and the user device 28 are described with respect to specific operations, it should be noted that the present embodiments described herein may be implemented in any suitable health-related data collection system. That is, the presently disclosed embodiments should not be limited the examples provided in FIG. 1. Instead, the embodiments described herein may be applied to any data collection system that collects health-related data of a user from a variety of entities.

It should be noted that the systems, devices, and components described above with regard to the user authentication system 10 are exemplary systems, devices, and components. The user authentication system 10 may include additional or fewer components as shown.

With the foregoing in mind, to enable the monitoring system 14 to verify the user identity based on user's health information, the wearable system 12 may use the one or more sensors 30 to acquire the user's health information. The acquired user's health information may be collected and transmitted to the monitoring system 14 via secured connections created by the network controller 44.

Figure 2:
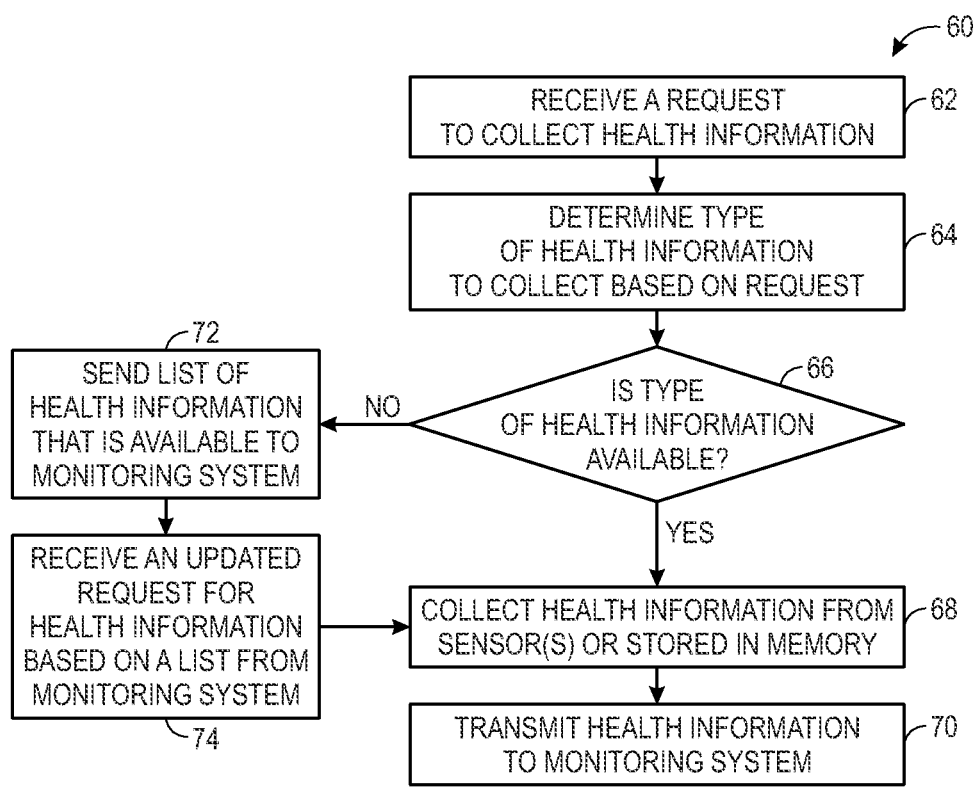
FIG. 2 illustrates a flow diagram of a method for collecting health information corresponding to a user in response to a request from the user authentication system of FIG. 1, in accordance with embodiments described herein.

For example, FIG. 2 illustrates a method 60 for collecting health information corresponding to a user in response to a request. Although the method 60 described in FIG. 2 is described in a particular order and as being performed by a particular component, it should be understood that the method may be performed in any suitable order and by any suitable computing device or application.

In an embodiment, the wearable system 12 may receive a request to collect health information (block 62) regarding a user wearing the wearable system 12. For example, the request may be initiated by a medical receptionist in a hospital or in a physician's office via a service system (e.g., the monitoring system 14) to collect health information for the user (e.g., patient) visiting the hospital or the physician for certain medical or health-related reasons. The requested health information may be used to verify the user's identity that may facilitate a process of admission to allow the user to receive corresponding medical treatment or health care service.

In response to receiving the request for the health information of the user, the wearable system 12 may determine one or more types of the health information to collect based on the request (block 64). In an embodiment, the wearable system 12 may determine that the request includes collecting cardiovascular information such as heart rate, blood pressure, blood sugar level, and blood flow via appropriate sensors. In another embodiment, the wearable system 12 may determine that the request includes collecting weight-related information, such as weight gain or loss within a certain amount of time (e.g., within the last thirty days).

With the determined type(s) of the health information, at block 66, the wearable system 12 may further determine whether the type of the health information is available. In an embodiment, the wearable system 12 may query, via the processor 32, available health information as acquired from the one or more sensor(s) (e.g., current blood pressure) or based on the types of sensors that are accessible to the processor 32. In another embodiment, the wearable system 12 may query, via the processor 32, available health information (e.g., heart rate change within the last thirty days, blood pressure data on a particular day) stored in the memory 34.

If, at block 66, the wearable system 12 determines that the type of the health information is available, the wearable system 12 may collect health information from the one or more sensors 30 or stored in the memory 34 (block 68) via the processor 32. In some embodiments, the processor 32 may request that corresponding sensors collect, organize, format, integrate or merge, and filter various health information to create the health information 16 that will be transmitted to the monitoring system 14. In some embodiments, the wearable system 12 may convert the health information 16 into the common format for the EMR 22 as described above.

At block 70, the wearable system 12 may transmit the health information 16 to the monitoring system 14. The health information 16 may be transmitted in one or more packets to the monitoring system 14. For example, certain cardiovascular information (e.g., blood pressure, blood sugar) may be sent in one packet, while the weight change within the last thirty days may be transmitted in a different packet.

If, at block 66, the wearable system 12 determines that the type of the health information is not available, the wearable system 12 may send a list of health information that is available to the monitoring system 14 (block 72). For example, the request received from the monitoring system 14 may include collecting cardiovascular information such as heart rate, blood pressure, blood sugar level, and blood flow. Through collecting data via the one or more sensors 30, the processor 32 may determine that the blood flow sensor is not available (e.g., malfunction). The wearable system 12 may then (block 74) send a list of available health information (e.g., blood pressure, blood sugar, weight change within the last thirty days) to the monitoring system 14.

In response to receiving the list of available health information from the wearable system 12, the monitoring system 14 may generate an updated request for health information (e.g., by excluding the blood flow information) based on a new list. The wearable system 12 may receive the updated request for health information based on the list from the monitoring system 14 (block 74). Accordingly, the wearable system 12 may perform the steps described above at blocks 68 and 70.

As described above, the health information (e.g., the health information 16) may be transmitted to the monitoring system 14 for determining the user identity. However, the health information 16 may not be uniquely tied to the user. For example, other users (e.g., patients) may have the same or similar health information (e.g., blood pressure, blood sugar) as the user. To determining the user's identity, additional information (e.g., EMR) may be used alongside the health information 16 for determining the user identity in an accurate and efficient manner.

Figure 3:
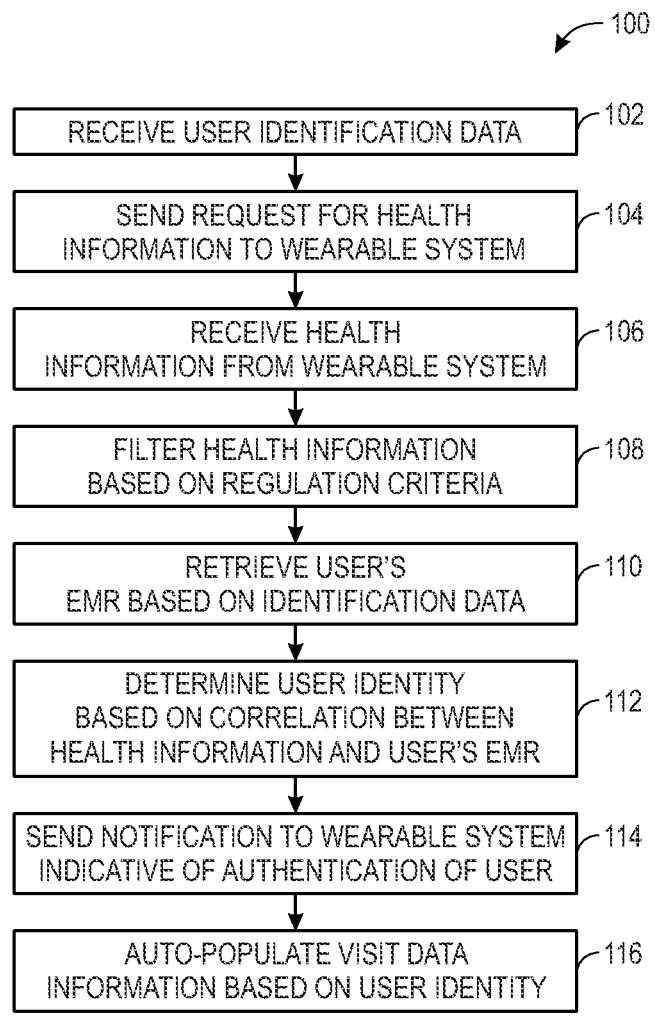
FIG. 3 illustrates a flow diagram of a method for determining a user's identity based on correlation(s) between user's health information and electronic medical record, in accordance with embodiments described herein.

With this in mind, FIG. 3 illustrates a flow diagram of a method 100 for determining a user's identity based on one or more correlations between the user's health information and EMR. Although the method 100 described in FIG. 3 is described in a particular order and as being performed by a particular component, it should be understood that the method 100 may be performed in any suitable order and by any suitable computing device or application.

Referring now to FIG. 3, the monitoring system 14 may receive user identification data (block 102). For example, a user (e.g., a patient) may visit a hospital or a physician office for medical or health-related reasons. The user may communicate with a medical receptionist to explain a purpose of visiting. The medical receptionist may request that the user to show certain identification document (e.g., driver license card) that may be used prove the user's identity. However, the requested identification document may not be available at the time of visiting. Alternatively, the user may wear a wearable system (e.g., the wearable system 12) that may be communicatively connected to the monitoring system 14, which may be a part of an admission system of the hospital or the physician's office. The medical receptionist may use received user identification data (e.g., name or other reference received via user input, image acquisition, etc.), the user's health information (e.g., the health information 16) collected from the wearable system 12, and the electronic medical record (e.g., EMR 22) associated with the user and other patients (e.g., who may have same names as the user) to determine the user's identity. That is, the user's identity may be determined based on his/her health information and medical record without using his/her identification document.

At block 104, the monitoring system 14 may send a request for health information to the wearable system 12. The request may be sent via a near field communication or any other suitable communication protocol. For example, after the user confirms that a wearable system (e.g., the wearable system 12) is available at the time of visiting, the medical receptionist may send the request for health information, via the communication interface 46 coupled to peripheral components, such as input devices (e.g., keyboard, mouse), to the wearable system 12 presently worn by the user.

After the wearable system 12 collects the requested health information, the monitoring system 14 may receive the health information (e.g., health information 16) transmitted from the wearable system 12 (block 106). The monitoring system 14 may use the processor 40 and instructions stored in the memory 42 to filter health information based on certain regulation criteria (block 108).

For example, the regulation criteria may be related to regulations such as the Health Insurance Portability and Accountability Act (HIPAA). According to HIPAA, there are 18 direct identifiers that are typically present in patient's medical records, including: names; geographic subdivisions smaller than a state (e.g. street address, city and ZIP code); all dates that are related to an individual (e.g., date of birth, admission), telephone numbers; fax numbers; email addresses; social security numbers; medical record numbers; health plan beneficiary numbers; account numbers; certificate/license numbers; vehicle identifiers and serial numbers, including license plate numbers; device identifiers and serial numbers; web universal locators (URLs); IP address numbers; biometric identifiers such as fingerprints and voice prints; full-face photographic images; and other unique identifying numbers, characteristics or codes.

Based on predetermined regulation criteria, the monitoring system 14 may filter the health information 16 by removing all information (e.g., direct identifiers) that can be used to identify the user from whose medical record the health information 16 may be related. Such information may be generated during collecting the requested heath information by the wearable system 12. For example, device identifiers and serial numbers associated with the wearable system 12 may be embedded into the health information 16. Thus, removing the identifiers and serial numbers may enable the collected data to correspond to regulations set by HIPAA.

As mentioned previously, the monitoring system 14 may retrieve the user's EMR based on the identification data (block 110). The identification data provided by the user may be used for querying the database 48 for EMRs that may be related to the identification data. For example, the EMRs may include cardiovascular information (e.g., heart rate, blood pressure, blood sugar level, and blood flow) associated with the user and/or other users (e.g., other patients vising the same physician and having similar identification data as the user). In some embodiments, the monitoring system 14 may retrieve additional health record from entities (e.g., the other entities 24) other than the EMR provider (e.g., the entity 20). For example, the additional health record may include weight-related information (e.g., weight gain or loss within the last thirty days) collected from a fitness center where the user may perform physical exercises to reduce his/her body weight. In addition, weight data may be received via a smart or communicatively coupled electronic scale that send the weight data to the monitoring system 14 or other suitable device.

After gathering information needed, the monitoring system 14 may determine user identity based on correlation(s) between the health information 16 and the user's EMR (block 112). For example, the monitoring system 14 may analyze, via the processor 40 and/or machine learning circuitry 50, the health information 16 that may include the user's cardiovascular information measured by the wearable system 12 in the last sixty days and multiple EMRs related to cardiovascular information recorded during office visit of different patients (including the user) within the last sixty days. By analyzing the correlations between the health information 16 and the EMRs, the monitoring system 14 may determine the user's identity. In some embodiments, the correlations may be determined based on a similarity analysis between the cardiovascular information recorded in the health information 16 and the EMRs.

In an embodiment, the user identity may not be determined or the determination may be associated with some uncertainty level (e.g., the similarity between the health information 16 and one EMR associated with the user is close to the similarity between the health information 16 and another EMR associated with a different user), the monitoring system 14 may request the wearable system 12 to collect additional information (e.g., gain or loss) within the last thirty days. For instance, the monitoring system 14 may also request fitness data from other data sources to collect information trend data within the last thirty days or some threshold amount of time. By analyzing the similarities between the additional information in the health information 16 and the two or more EMRs that may be close to each other, the monitoring system 14 may determine the user's identity by differentiating the user's additional information from the other users' records.

After the user's identity is determined, the monitoring system 14 may send a notification to the wearable system 12 indicative of authentication of the user (block 114). The monitoring system 14 may, in some embodiments, auto-populate visit data information in response to the user's identity being authenticated (block 116). For example, the auto-populated visit data information may include appointment corresponding to the user, user's insurance information, information regarding putting the user in the queue for a doctor visit, and the like.

In some cases, a user may attempt to access his/her personal data, such as EMR, health insurance record, or other health-related information in certain database(s) that may involve advanced user authentication. For example, the user may be requested to provide health information that may be collected from a wearable system worn by the user. In addition to the requested health information, the user may also be requested to provide additional personal information that may be used for verifying user identity. That is, to better ensure that the user's identity is authenticated, the health data authentication techniques described above may be supplemented using a multi-factor user authentication process.

Figure 4:
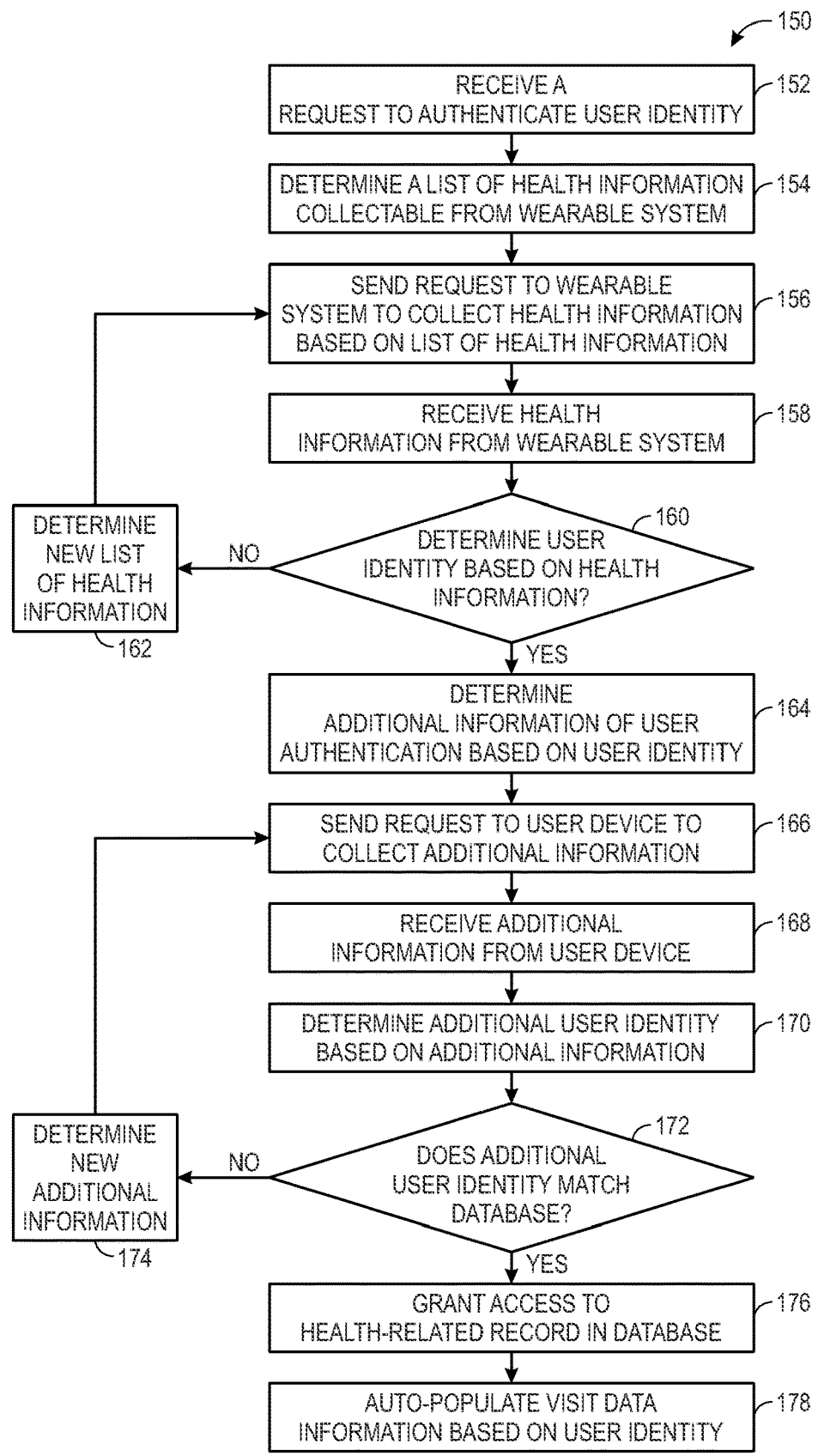
FIG. 4 illustrates a flow diagram of method for identity verification using a multi-factor user authentication process, in accordance with embodiments described herein.

With this in mind, FIG. 4 illustrates a flow diagram of method 150 for performing identity verification using a multi-factor user authentication process. The multi-factor user authentication process may be performed by the monitoring system 14 or any suitable computing system. Although the method 150 described in FIG. 4 is described in a particular order and as being performed by a particular component, it should be understood that the method may be performed in any suitable order and by any suitable computing device or application.

At block 152, the monitoring system 14 may receive a request to authenticate user identity. For example, in response to a user request to access his/her EMR or other health-related information in its database(s), an entity that may hold the user's information may send the request to authenticate user identity to the monitoring system 14.

In response to receiving the request to authenticate user identity, the monitoring system 14 may determine a list of health information collectable from a wearable system (block 154). For example, the wearable system may be the wearable system 12 worn by the user requesting to access his/her EMR or other health-related information. In an embodiment, the list may include cardiovascular information such as heat rate, blood pressure, blood sugar level, and blood flow.

At block 156, the monitoring system 14 may send the request to the wearable system to collect health information based on the list of health information. In response to the received request, the wearable system may query available health information (e.g., current heart rate or blood pressure) from one or more sensor(s). The wearable system may then transmit the collected health information to the monitoring system 14.

The monitoring system 14 may receive the health information from the wearable system (block 158) and determine user identity based on the received health information (block 160). If, for example, due to the limited content or scope of the received health information the monitoring system 14 may not be able to determine the user identity, or may determine the user identity but with uncertainty, the monitoring system 14 may determine a new list of health information (block 162) and sent the new list to the wearable system (returning to block 156 as shown). In an embodiment, the initial list of health information may include a request for the user's heart rate, blood pressure, blood sugar level, and blood flow. The new list may exclude the blood flow, which may not be available based on the received health information.

If the user identity can be determined based on the health information received from the wearable system, the monitoring system 14 may determine additional information of the user authentication based on the user's identity (block 164). For example, the additional information may be related to the user's feedback to certain security questions, such as properties and/or vehicles currently and/or previously owned, schools attended, places visited, doctors and/or hospitals visited, and the like.

At block 166, the monitoring system 14 may send a request to a user device (e.g., the user device 28) to collect the additional information. The user device may be a portable computing device such as a smartphone, tablet, electronic glass, wearable device, implanted computer, automotive computer, and so forth. In some embodiments, the user device may be a less portable type of computing device, such as a desktop computer, laptop computer, game console, smart appliance, and so forth.

The monitoring system 14 may then receive the additional information from the user device (block 168) and determine an additional user identity based on the additional information (block 170). For example, the monitoring system 14 may review the user's feedback to certain security questions with respect to references (e.g., correct answers) in the database(s).

Based on the additional user identity, at block 172, the monitoring system 14 may determine whether the additional user identity matches user's identity information stored in the database(s). If the additional user identity does not match the user's identity information in the database, the monitoring system 14 may determine new additional information (block 174) and send a new request containing the new additional information to the user device (returning to block 166 as shown).

If the additional user identity matches the user's identity information stored in the database, the monitoring system 14 may further authenticate the identity of the user and grant access to health-related record in the database (block 176). For example, the user may be granted to access his/her personal data, such as EMR, health insurance record, or other health-related information in the database(s) requiring advanced user authentication as described above.

Further, the monitoring system 14 may auto-populate visit data information based on the user identity (block 178). For example, the auto-populated visit data information may include appointment corresponding to the user, user's insurance information, information regarding putting the user in the queue for a doctor visit, and the like. In some embodiments, the monitoring system 14 may retrieve information associated with the user from a database in response to authenticating the identity of the user. Such information may include the auto-populated visit data information.

The technologies described in the disclosed embodiments include verifying user identity based on correlations between user's health information collected from a wearable system and user's electronic medical record (EMR). The use of physical identity documents may be avoided because the technologies described herein may involve the use of a wearable system that may be carried by the user all the time. As the health information collected from wearable system may constantly change over the time, the resulting identity verification is based on dynamically generated security features that are safer to use than static security methods (e.g., physical IDs) or more convenient to use than certain dynamic security methods (e.g., constantly update passwords).

In addition to verifying the user identity using health information collected from a wearable system, the multi-factor user authentication process disclosed herein may provide an advanced security mechanism for verifying the user's identity by requesting multiple credentials (e.g., dynamically changed biomedical information and additional security questions) rather than just asking identity documents, usernames and passwords, which may be vulnerable to malicious use of the user's personal information (e.g., faked IDs, identity theft, and the like). A user device may be used for providing additional credentials. With extra layers of security added by the multi-factor user authentication process, user's privacy data may receive improved protections against various malicious use of the user's personal information while in complying with privacy-related regulations such as HIPAA.

While only certain features of disclosed embodiments have been illustrated and described herein, many modifications and changes will occur to those skilled in the art. It is, therefore, to be understood that the appended claims are intended to cover all such modifications and changes as fall within the true spirit of the present disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A system, comprising:
a first computing device configured to send a request for identification data, wherein the identification data corresponds to one or more health properties associated with a user; and
a second computing device configured to perform operations comprising:
receiving the request for the identification data;
determining a type of health data that corresponds to the one or more health properties;
in response to determining that the type of health data is accessible to the second computing device:
retrieving health data from a memory, wherein the health data is acquired by one or more sensors for monitoring the one or more health properties that correspond to the user; and
sending the health data to the first computing device, wherein the first computing device is configured to authenticate an identity of the user based on the health data;
in response to determining that the type of health data is inaccessible to the second computing device:
send a list of types of health data to the first computing device, wherein the list of types of health data is accessible to the second computing device;
receive an additional request for the identification information, wherein the additional request comprise additional health data associated with the list of types of health data;
retrieving the additional health data from the memory; and
sending the additional health data to the first computing device, wherein the first computing device is configured to authenticate the identity of the user based on the additional health data.

2. The system of claim 1, wherein the one or more sensors comprise one or more motion sensors, one or more thermal sensors, one or more temperature sensors, one or more imaging sensors, one or more biomedical sensors, one or more proximity sensors, one or more pressure sensors, one or more position sensors, one or more electrical sensors, one or more optical sensors, one or more photoelectric sensors, one or more contact sensors, one or more non-contact sensors, or any combination thereof.

3. The system of claim 1, wherein the first computing device is configured to authenticate the identity of the user by correlating the health data with one or more electronic medical records stored in one or more databases.

4. The system of claim 3, wherein correlating the health data with the one or more electronic medical records comprises identifying one or more similarities between the health data and the one or more electronic medical records.

5. The system of claim 4, wherein the first computing device comprises a machine learning circuitry configured to perform identifying the one or more similarities.

6. The system of claim 1, wherein the second computing device comprises a wearable device.

7. The system of claim 6, wherein the wearable device is configured to reformat the health data into a different format.

8. The system of claim 1, wherein the first computing device comprises a network controller configured to establish a secure communication connection between the first computing device and the second computing device.

9. The system of claim 8, wherein the secure communication connection is established based on one or more public cryptographic keys, one or more private cryptographic keys, one or more ciphers, one or more digital certificates, one or more credentials supported by a security protocol, or any combination thereof.

10. A method, comprising:
receiving, via a processor, identification data associated with a user;
sending, via the processor, a request for health data to a wearable system based on the identification data, wherein the wearable system comprises a plurality of sensors configured to acquire the health data indicative of one or more health properties corresponding to the user;
receiving, via the processor, a list of types of health data available to the wearable system in response to the health data being inaccessible to the wearable system;
sending, via the processor, an additional request for the identification data to the wearable system, wherein the additional request comprises additional health data associated with the list of types of health data;
receiving, via the processor, the additional health data from the wearable system;
retrieving, via the processor, a plurality of electronic medical records based on the identification data;
determining, via the processor, an identity of the user based on one or more correlations between the health data and the plurality of electronic medical records; and
sending, via the processor, a notification indicative of an authentication of the user to the wearable system in response to determining the identity of the user.

11. The method of claim 10, wherein the identification data comprises a name or other reference data associated with the user.

12. The method of claim 10, comprising:
modifying the additional health data to remove one or more identifiers associated with the user; and
determining the identity of the user based on the one or more correlations between the modified additional health data and the plurality of electronic medical records.

13. The method of claim 10, comprising retrieving, via the processor, a set of health data to determine the identity of the user based on two or more users having the one or more correlations.

14. The method of claim 10, wherein the additional health data comprises cardiovascular information associated with the user.

15. The method of claim 10, wherein the plurality of electronic medical records is previously modified to exclude one or more identifiers associated with the user.

16. The method of claim 15, wherein the one or more identifiers comprise one or more names, one or more addresses, one or more telephone numbers, one or more fax numbers, one or more email addresses, one or more social security numbers, one or more medical record numbers, one or more health plan beneficiary numbers, one or more account numbers, one or more certificate numbers, one or more license numbers, one or more vehicle identification numbers, one or more device serial numbers, one or more web universal locators, one or more IP addresses, one or more biometric identifiers, one or more full-face photographic images, or any combination thereof.

17. A non-transitory computer-readable medium comprising computer-executable instructions that, when executed by a processor, cause the processor to:
receive a first request to authenticate an identity of a user;
send a second request to a wearable system to collect health data based on one or more health properties associated with the user, wherein the health data is determined based on the first request;
receive a list of types of health data available to the wearable system in response to the health data being inaccessible to the wearable system;
send an additional request for the identification data to the wearable system, wherein the additional request comprises additional health data associated with the list of types of health data;
receive the additional health data from the wearable system; and
determine the identity of the user based on the additional health data.

18. The non-transitory computer-readable medium of claim 17, wherein the computer-executable instructions that, when executed by the processor, causes the processor to:
determine additional data accessible via the wearable system associated with user authentication based on the identity of the user, wherein the additional data comprises one or more factors for verifying the identity of the user;
send a third request to a user device to collect the additional data;
receive the additional data from the user device;
determine additional identity information of the user based on the additional data from the user device;
determine whether the additional identity information match the identity of the user; and
in response to determining the additional identity information match the identity of the user, authenticate the identity of the user to allow the user to access one or more electronic medical records stored in one or more databases.

19. The non-transitory computer-readable medium of claim 18, wherein the instructions are configured to cause the processor to:
retrieve information associated with the user from a database in response to authenticating the identity of the user; and
populate one or more data entry fields of one or more forms based on the information associated with the user in response to authenticating the identity of the user.

* * * * *